United States Patent [19]

Singh

[11] 4,321,427

[45] Mar. 23, 1982

[54] APPARATUS AND METHOD FOR AUDIOMETRIC ASSESSMENT

[76] Inventor: Sadanand Singh, c/o University of Texas, Health Science Center of Houston, 1343 Moursund, Houston, Tex. 77030

[21] Appl. No.: 76,608

[22] Filed: Sep. 18, 1979

[51] Int. Cl.³ ............................................. A61B 5/12
[52] U.S. Cl. .................................... 179/1 N; 128/746
[58] Field of Search ......................... 179/1 N; 128/746

[56] References Cited

U.S. PATENT DOCUMENTS

| | | | |
|---|---|---|---|
| 2,229,206 | 1/1941 | Cubert | 179/1 N |
| 3,721,764 | 3/1973 | Dunn | 179/1 N |
| 4,099,035 | 7/1978 | Yanick | 179/1 N |
| 4,139,730 | 2/1979 | Franklin | 179/1 N |

FOREIGN PATENT DOCUMENTS

| | | | |
|---|---|---|---|
| 2806626 | 8/1979 | Fed. Rep. of Germany | 179/1 N |
| 2296397 | 7/1976 | France | 179/1 N |

*Primary Examiner*—Stuart N. Hecker

[57] ABSTRACT

An apparatus for producing sounds of selectable pitch, quality and sound pressure level and a method for using the apparatus in assessing a person's hearing are disclosed. The apparatus includes a function generator for generating the fundamental frequency of the sound to be produced, a formant filter circuit for passing only one or more resonant frequencies of the fundamental frequency so as to vary the quality of the sound to be produced, and a level control for varying the loudness of the sound to be produced. The method of the invention includes adjusting the apparatus of the invention so as to produce sounds similar to those a patient produces in his own speech and using such sounds to assess the patient's hearing skills.

28 Claims, 13 Drawing Figures

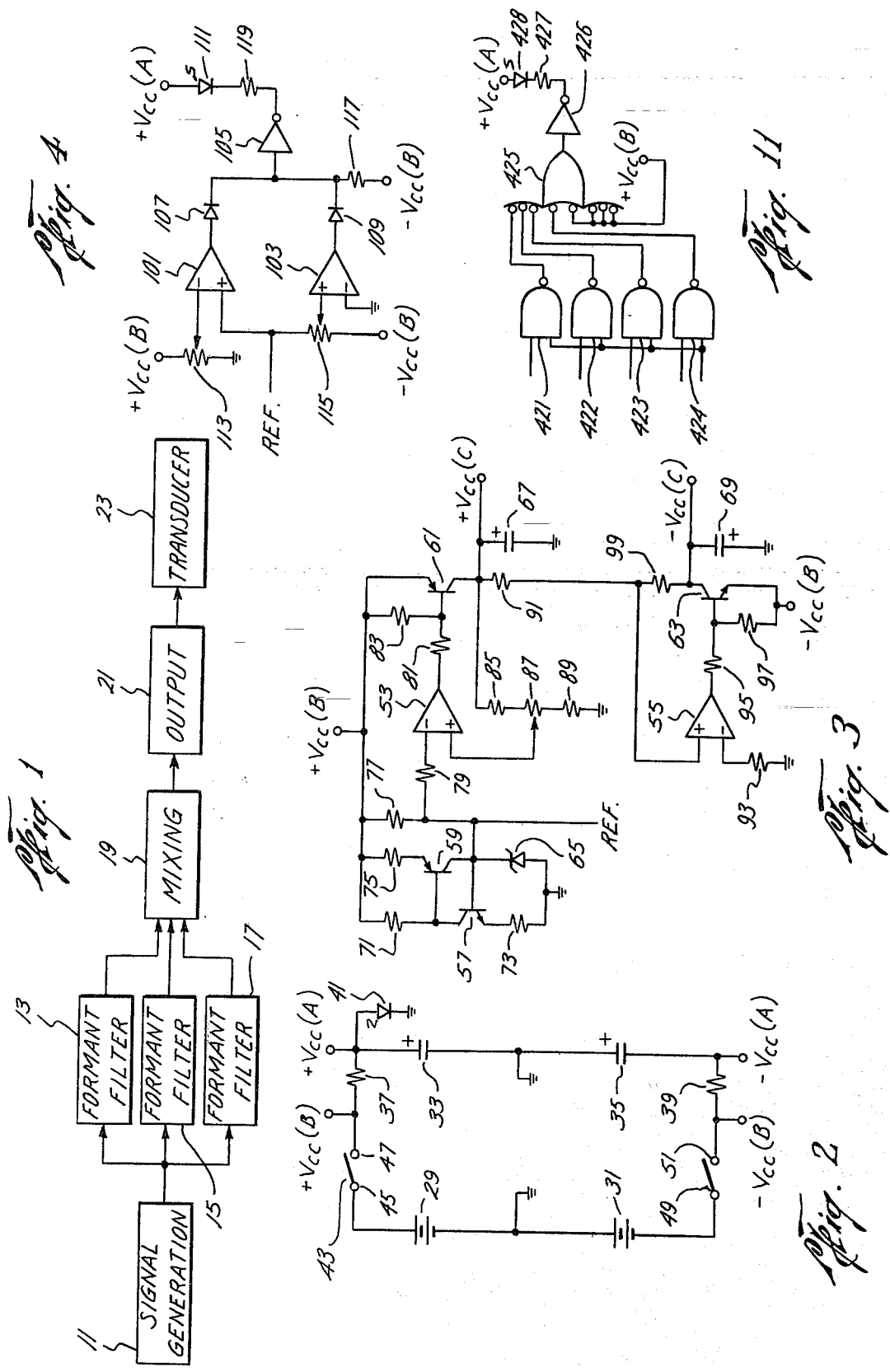

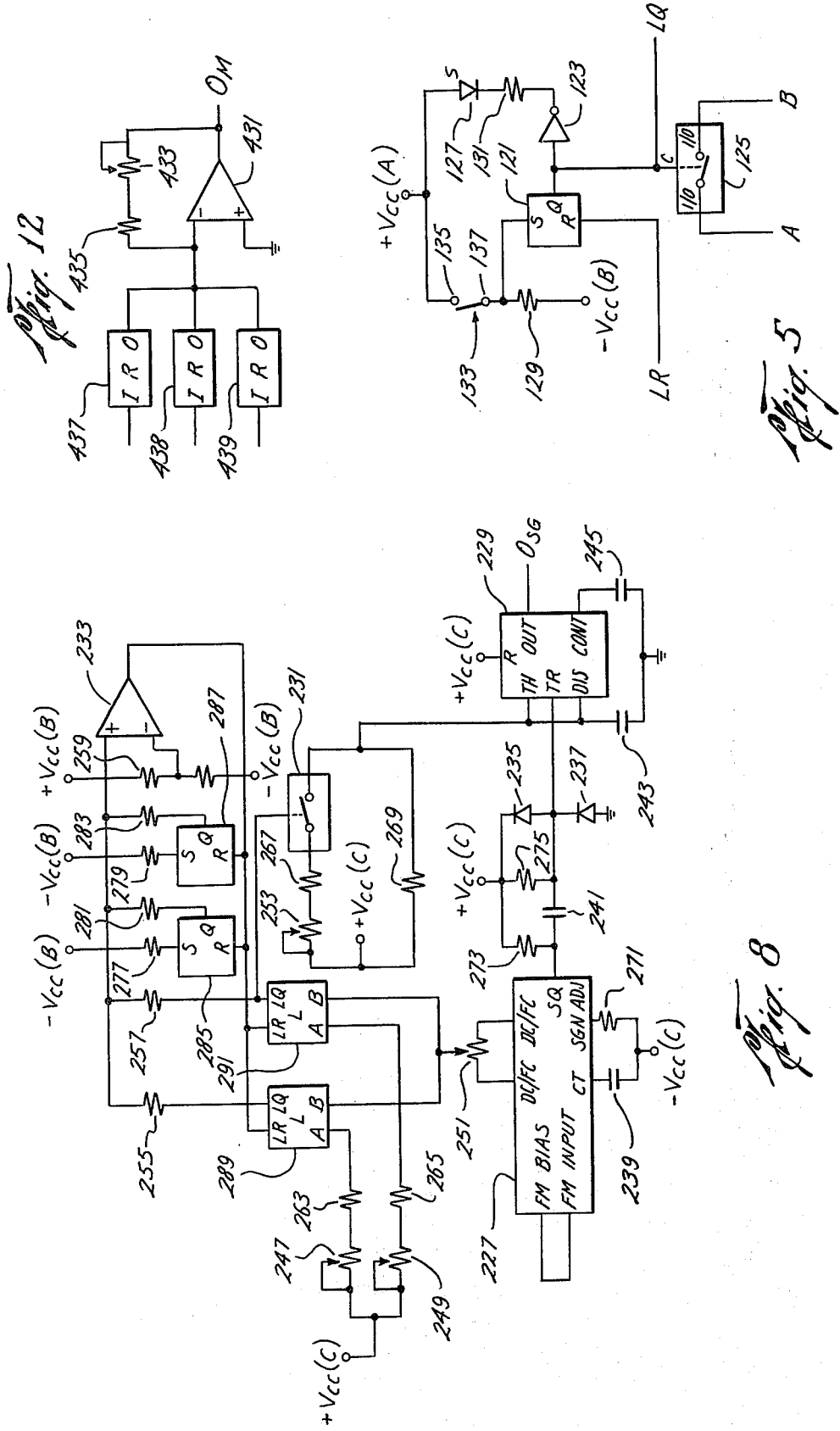

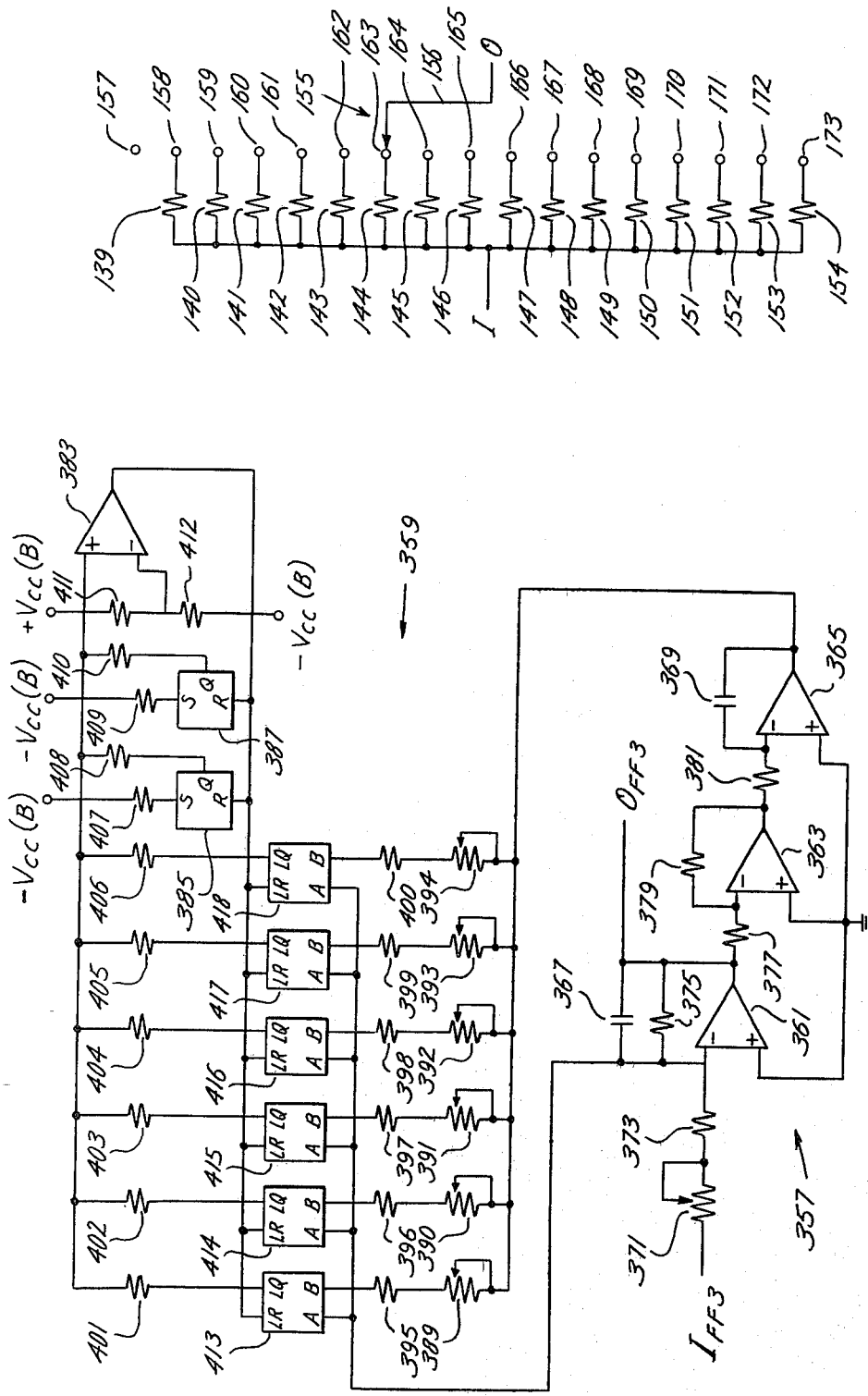

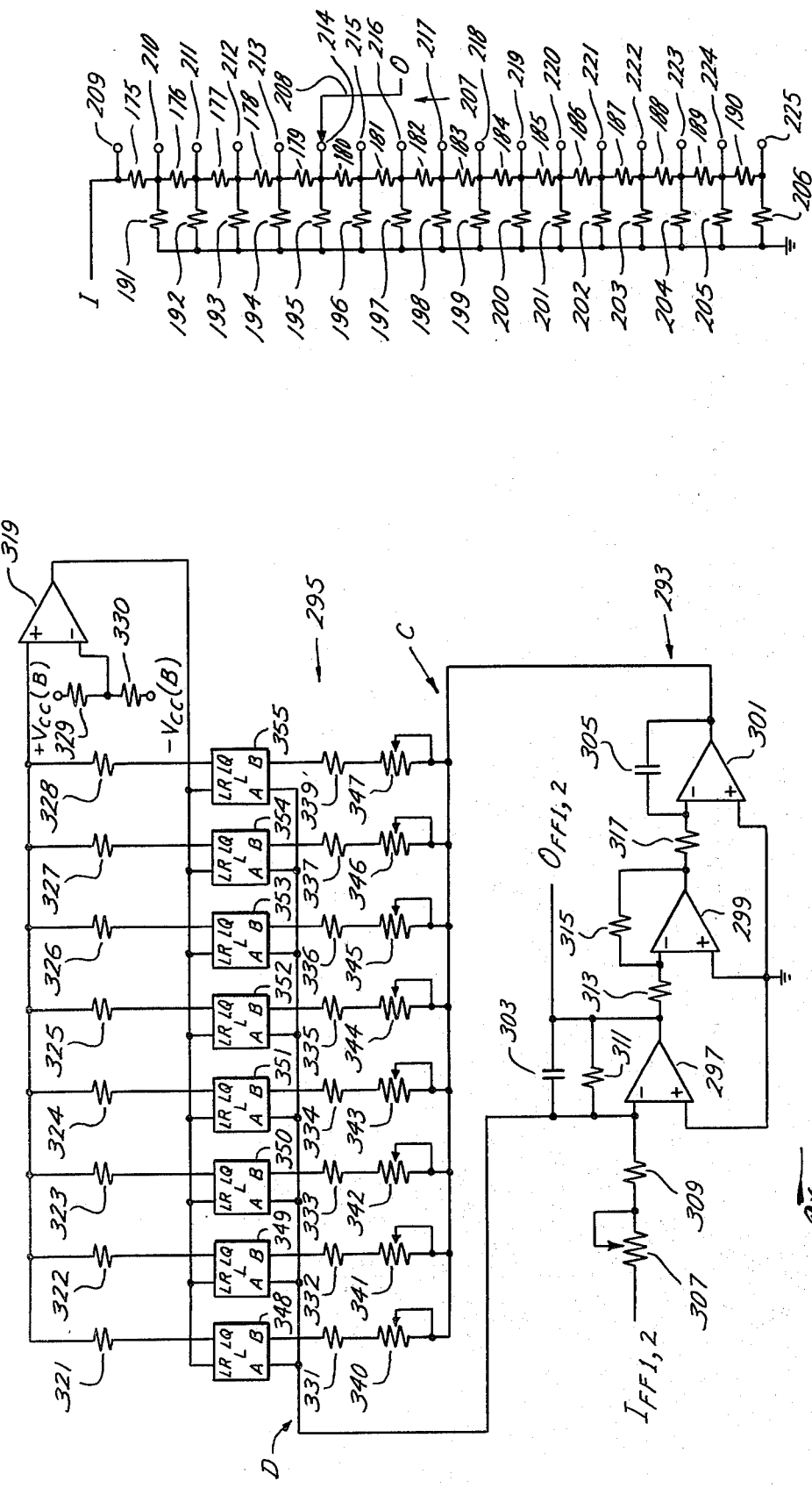

APPARATUS AND METHOD FOR AUDIOMETRIC ASSESSMENT

BACKGROUND OF THE INVENTION

1. Field of the Invention

The present invention relates generally to apparatus and methods used in assessing a person's hearing acuity and more specifically to audiometric apparatus and methods that produce and involve the production of synthetic speech sounds.

2. Description of the Prior Art

Traditionally, the evaluation of a person's hearing acuity and the determination of the site of lesion in persons with auditory pathologies has been accomplished in the field of audiology using an audiometer that can be operated in either a pure-tone or speech mode. While in the pure-tone mode, such an audiometer, known as a pure-tone and speech audiometer, is capable of producing pure tones, i.e., tones of a single frequency, at octave intervals. The frequency, sound pressure level (SPL) and the duration of such tones are controllable by the operator of the audiometer. According to ordinary audiological techniques involving the production of pure tones, the patient is asked to give a signal whenever he hears a pure tone generated by the audiometer. While the audiometer is in the speech mode, the operator of the audiometer pronounces common words, usually one or two syllable words, into a microphone. The sound of such words is reproduced by the audiometer in substantially their original form although the loudness of the reproduced sound is controllable by the operator. According to standard audiological techniques, the patient is requested to identify the word reproduced by the audiometer.

Many pure-tone and speech audiometers are also capable of producing white noise simultaneously with or separate from the speech or pure-tone sounds. Ordinarily, such white noise is used to mask the pure tone or speech sounds in order to evaluate the patient's ability to discriminate such sounds from the white noise.

A problem with the pure-tone and speech audiometer is that it basically assesses audition using only a very rudimentary (pure-tone) or an extremely complex (speech) sound. Such an audiometer and the techniques associated therewith provide little flexibility for evaluating a person's auditory behavior between those two levels of functioning. Thus, while such an audiometer is sufficient to provide audiometric data for the majority of patients seen in a routine diagnostic examination, something more is needed for other patients such as those that are difficult to test, those with a severe or profound hearing impairment and those with central auditory processing problems. In addition, the specific frequencies used for testing with such an audiometer may not be those to which these special cases are most sensitive.

SUMMARY OF THE INVENTION

The present invention is an improved audiometer that is capable of producing sounds essentially throughout the range of complexity between pure-tone sounds and speech sounds as well as a method for using such an improved audiometer in assessing a person's hearing skills. In addition, the apparatus of the present invention is capable of producing sounds similar to those produced in the patient's own speech.

The apparatus of the present invention includes circuitry for generating an electrical signal of selectable complexity and amplitude. This signal can then be applied to one or more transducers to produce a sound of a particular fundamental frequency, quality and loudness. Such circuitry includes a generator for producing a single-frequency signal, such frequency being selectably variable, and filter circuitry for passing only one or more harmonics of the signal produced by such generator on such signal. The amplitude of each of such harmonics, as well as their frequencies, is selectably variable.

BRIEF DESCRIPTION OF THE DRAWINGS

For a further understanding of the nature and objects of the present invention, reference should be made to the following detailed description, taken in conjunction with the accompanying drawings, in which like parts are given like reference numerals and wherein:

FIG. 1 is a schematic block diagram of the preferred embodiment of the apparatus of the invention further showing the connection of such apparatus to a transducer;

FIG. 2 is an electronic schematic diagram of the power source circuit of the preferred embodiment of the apparatus of the invention;

FIG. 3 is an electronic schematic diagram of the power regulation circuit of the preferred embodiment of the apparatus of the invention;

FIG. 4 is an electronic schematic diagram of the low battery indication circuit of the preferred embodiment of the apparatus of the invention;

FIG. 5 is an electronic schematic diagram of a latching circuit of the preferred embodiment of the apparatus of the invention;

FIG. 6 is a schematic diagram of a resistor switch circuit of the preferred embodiment of the apparatus of the invention;

FIG. 7 is an electronic schematic diagram of the divider switch of the preferred embodiment of the apparatus of the invention;

FIG. 8 is an electronic schematic diagram of the signal generation circuit of the preferred embodiment of the apparatus of the invention;

FIG. 9 is an electronic schematic diagram of one configuration of a formant filter circuit of the preferred embodiment of the apparatus of the invention;

FIG. 10 is an electronic schematic diagram of another configuration of a formant filter circuit of the preferred embodiment of the apparatus of the invention;

FIG. 11 is an electronic schematic diagram of the illegal combination detection circuit of the preferred embodiment of the apparatus of the invention;

FIG. 12 is an electronic schematic diagram of the mixing circuit of the preferred embodiment of the apparatus of the invention.

DETAILED DESCRIPTION OF THE PREFERRED EMBODIMENT

1. Functional Description of the Apparatus

Figure 13:
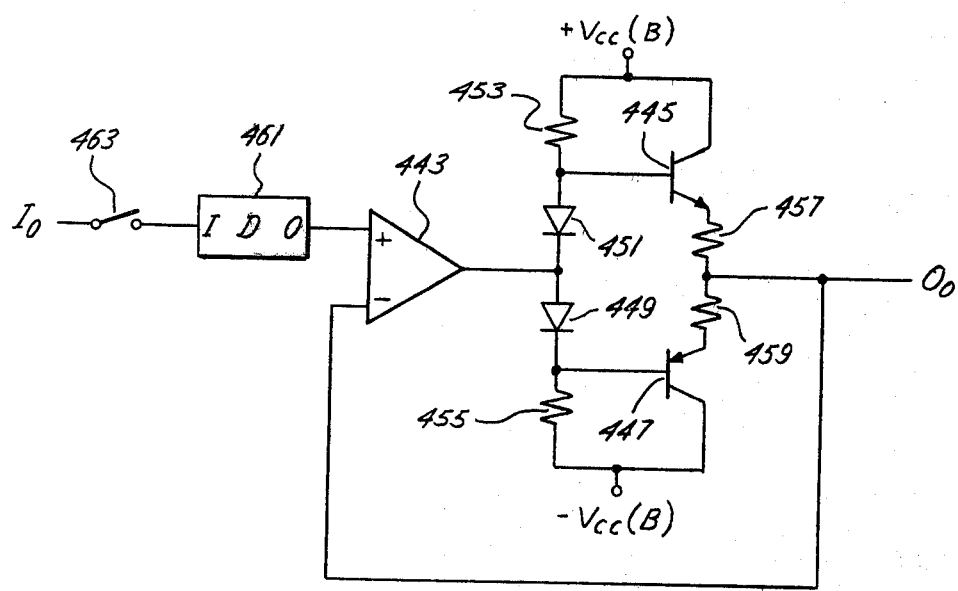
FIG. 13 is an electronic schematic diagram of a channel of the output circuit of the preferred embodiment of the apparatus of the invention.

Generally speaking, the apparatus of the invention produces sounds of selectable pitch, quality and sound pressure level. Such sounds are produced by generating an electrical signal having (1) a fundamental component of selectably-variable frequency and (2) one or more harmonic terms of selectably-variable frequency and amplitude. The amplitude of the overall signal also is selectably variable. This signal is applied to a transducer for converting the electrical signal into sound. Thus, variation of the pitch of the sound is accomplished by varying the frequency of the fundamental component of the electrical signal; variation of the quality of the sound is accomplished by varying the frequencies and amplitudes of the harmonic terms of the electrical signal; and variation of the loudness of the sound is accomplished by varying the amplitude of the overall signal.

The generation and control of the electrical signal is accomplished by an electronic circuit that, in the preferred embodiment, includes the following functional subcircuits (see FIG. 1): signal generation circuit 11, formant filter circuits 13, 15, 17, mixing circuit 19 and output circuit 21. The signal at the output of circuits 21 is applied to transducer unit 23. Power is supplied to the functional subcircuits by a battery-powered power supply (not shown in FIG. 1).

Generation circuit 11 generates a signal that includes the fundamental component and substantially all the harmonics of such fundamental component in a substantially flat spectrum. Preferably, the frequency of such signal is variable among two or more frequencies substantially corresponding to the average frequency of the fundamental of speech sounds produced by various identifiable groups of people, such as adult men on one hand and women and children on another hand. Generation circuit 11 includes means for varying the frequency of the fundamental component such that the energy of the signal generated by circuit 11 remains substantially constant regardless of the frequency of the fundamental component.

The signal generated by generation circuit 11 is applied simultaneously to each of formant filter circuits 13, 15, 17. Each formant filter circuit includes a bandpass filter that filters all but one of the harmonic terms from the electrical signal generated by generation circuit 11. Thus, the signal at the output of each format circuit will include, in essence, only the fundamental component and one harmonic term of the signal generated by generation circuit 11. The frequency of the harmonic term included in the signal at the output of a formant filter circuit will correspond to the center frequency of the bandpass filter of the formant filter circuit. The center frequency of formant filter circuits 13, 15, 17 are variable over a first, second and third frequency range, respectively. The first, second and third frequency ranges correspond generally to the first, second and third formants, respectively, for average voices.

The signals at the outputs of formant filter circuits 13, 15, 17 are applied in parallel to mixing circuit 19 which includes a mixer for combining such signals into a single signal that includes the fundamental component and the harmonic term passed by the bandpass filters of at least one of the formant filter circuits. Mixing circuit 19 further includes means for varying the relative amplitudes of the harmonic terms in the signal at the output of the mixer and for selectably disconnecting the output of the formant filter circuits from the mixer.

The signal at the output of mixing circuit 19 is applied to output circuit 21. Output circuit 21 provides variable amplitude and power gain to the signal supplied by mixing circuit 19 so as to produce a signal capable of driving the transducers of transducer unit 23. In the preferred embodiment, the gain of output circuit 21 corresponds to transducer unit 23 such that the sound pressure level of the sound produced by transducer unit 23 is variable over a wide range of audible levels beginning at 0 db. Furthermore, in the preferred embodiment, output circuit 21 includes two separate channels each having independently variable gain, the signal at the output of mixing circuit 19 being applied simultaneously to each channel. The output of each channel is provided to a separate transducer of transducer unit 23. The circuit configuration of the channels of output circuit 21 is substantially identical so that the pitch and quality of the sounds produced by the transducers of transducer unit 23 are substantially the same, although the sound pressure level of such sounds may be varied with respect to one another.

Also, in the preferred embodiment, each channel of the output circuit has a switch at its input for controlling the application of an electrical signal to the transducers of the transducer unit.

2. Specific Component Configuration

The above-described functional circuits of the apparatus of the invention and the power supply for supplying power to such subcircuits may comprise any of a wide variety of component configurations which are now known in the art. Certain component arrangements for such subcircuits and such power supply, however, have been found to provide especially desirable results for accomplishing their particular function both as an individual unit and as part of the entire apparatus. Such component arrangements are shown in FIGS. 2–13 and will be described with respect thereto.

It should be noted that the particular component configurations shown and described include numerous integrated circuit chips. As is well known in the art of electronics, each such chip must be separately supplied with power. Furthermore, depending on the type of the chip, a single chip may include one or more substantially independent functional units. Where there is more than one unit on a single chip, each unit on the chip is substantially identical to one another. In order to facilitate an understanding of the operation of the particular component configurations, the functional units are shown and identified as a single unit using symbols and terms recognized in the art. In addition, each such unit will initially be identified as being all or part of a chip having a particular type number. The precise pin connections for such units as well as the pin connections for supplying power to the chips and the potential applied to such connections are set forth in the appendix to this description.

A. Power supply

As with any electronic apparatus, the power supply for supplying power to the functional circuitry is dictated to a large extent by the particular component configuration of such functional circuitry. Therefore, the particular power supply described herein is designed to meet the requirements of the particular component configurations set forth hereinafter for the functional subcircuits of the preferred embodiment of the invention. In accordance with such requirements, the power supply of the preferred embodiment is battery powered and provides unregulated voltages of +6VDC and −6VDC with respect to a common circuit ground, and regulated voltages of +5VDC and −5VDC with respect to the same ground. Because, as set forth infra, the preferred embodiment of the invention includes numerous light emitting diodes (LEDs) for indication purposes, the unregulated voltages are both split into a first and second portion, one portion for powering the LEDs and the remaining portion for powering other circuitry. In this way, the LEDs will not excessively load the power supply to the remainder of the circuit. Hereinafter, the unregulated voltage supplied to the LEDs is identified as $+V_{cc}(A)$ and $-V_{cc}(A)$, the unregulated voltage supplied to the remainder of the circuit is identified as $+V_{cc}(B)$ and $-V_{cc}(B)$, and the regulated voltage is identified as $+V_{cc}(C)$ and $-V_{cc}(C)$.

In accordance with the foregoing, the power supply of the preferred embodiment of the apparatus of the invention includes three circuits: (1) a power source circuit for providing the unregulated power ($+Vcc(A)$, $-Vcc(A)$, $+Vcc(B)$ and $-Vcc(B)$) for the apparatus; (2) a power regulation circuit for providing regulated power ($+Vcc(A)$ and $-Vcc(A)$) for the apparatus; and (3) a low battery indication circuit for indicating that the voltage of at least one of the batteries of the power source circuit is below a particular, predetermined value.

Referring to FIG. 2, the power source circuit includes the following components:

| Component Name | Reference Number | Preferred Type or Value |
| --- | --- | --- |
| Battery (6 Volt) | 29 | Burgess F4BP |
| Battery (6 Volt) | 31 | Burgess F4BP |
| Capacitor (Electrolytic) | 33 | 1000 mfd at __ VDC |
| Capacitor (Electrolytic) | 35 | 1000 mfd at __ VDC |
| Resistor | 37 | 22 ohm |
| Resistor | 39 | 22 ohm |
| Light-Emitting Diode (LED) | 41 | 1N __ |

The power source circuit further includes double-pole singlethrow switch 43 having terminals 45, 47 at one pole and terminals 49, 51 at the other pole.

The components of the power source circuit are interconnected as follows: the negative side of battery 29 and the positive side of battery 31 are connected together and constitute circuit ground. The positive side of battery 29 is connected to terminal 45 of switch 53. The negative side of battery 31 is connected to terminal 49 of switch 43. Terminal 47 of switch 43 is connected to one end of resistor 37. Terminal 51 of switch 43 is connected to one end of resistor 39. The other end of resistor 37 is connected to the cathode of diode 41 and to the positive side of capacitor 33. The other end of resistor 39 is connected to the negative side of capacitor 35. The negative side of capacitor 33 and the positive side of capacitor 35 are connected to circuit ground.

According to the operation of the power source circuit, when switch 43 is closed, +6VDC will be provided at either end of resistor 37 and −6VDC will be provided at either end of resistor 39. Thus, $+V_{cc}(A)$ is provided at the end of resistor 37 connected to capacitor 33, $+V_{cc}(B)$ is provided at the end of resistor 37 connected to terminal 47, $-V_{cc}(A)$ is provided at the end of resistor 39 connected to capacitor 35, and $-V_{cc}(B)$ is provided at the end of resistor 39 connected to terminal 51. In addition, when switch 43 is closed, LED 41 will be forward biased by $+V_{cc}(A)$ and, therefore, will be illuminated indicating that the power is on.

Referring to FIG. 3, the power regulation circuit includes the following components:

| Component Name | Reference Number | Preferred Type or Value |
| --- | --- | --- |
| Operational Amplifier | 53 | ½ 1458 |
| Operational Amplifier | 55 | ½ 1458 |
| NPN Transistor | 57 | 2 N 4123 |
| PNP Transistor | 59 | 2 N 4125 |
| PNP Transistor | 61 | 2 N 4125 |
| NPN Transistor | 63 | 2 N 4123 |
| Zener Diode | 65 | 1 N 5523 |
| Capacitor (Electrolytic) | 67 | 10 mfd at __ VDC |
| Capacitor (Electrolytic) | 69 | 10 mfd at __ VDC |
| Resistor | 71 | 1.5 Kohm |
| Resistor | 73 | 1.5 Kohm |
| Resistor | 75 | 100 ohm |
| Resistor | 77 | 27 Kohm |
| Resistor | 79 | 5.1 Kohm |
| Resistor | 81 | 2.2 Kohm |
| Resistor | 83 | 330 ohm |
| Resistor | 85 | 3.9 Kohm |
| Potentiometer | 87 | 2 Kohm |
| Resistor | 89 | 3.9 Kohm |
| Resistor | 91 | 10 Kohm |
| Resistor | 93 | 5.1 Kohm |
| Resistor | 95 | 2.2 Kohm |
| Resistor | 97 | 330 ohm |
| Resistor | 99 | 10 Kohm |

The components of the power regulation circuit are interconnected as follows: one end of resistors 71, 75, 77, 83 and the emitter of transistor 61 are connected to $+Vcc(B)$. The other end of resistor 71 is connected to the base of transistor 59 and to the collector of transistor 51. The other end of resistor 75 is connected to the emitter of transistor 59. The collector of transistor 59 is connected to the base of transistor 57, the anode of diode 65, and to one end of resistors 77, 79. The emitter of transistor 57 is connected to one end of resistor 73. The other end of resistor 73 and the cathode of diode 65 are connected to circuit ground. The other end of resistor 79 is connected to the inverting input of amplifier 53. The non-inverting input of amplifier 53 is connected to the arm of potentiometer 87. The output of amplifier 53 is connected to one end of resistor 81. The other end of resistor 81 is connected to end of resistor 83 and the base of transistor 61. The collector of transistor 61 is connected to the positive side of capacitor 67, to one end of resistor 91, and to one end of resistor 85. The other end of resistor 85 is connected to one end of potentiometer 87. The other end of potentiometer 87 is connected to one end of resistor 89. The other end of resistor 89 is connected to circuit ground. The negative side of capacitor 67 is connected to circuit ground. The other end of resistor 91 is connected to one end of resistor 99 and to the non-inverting input of amplifier 55. The inverting input of amplifier 55 is connected to one end of resistor 93. The other end of resistor 93 is connected to circuit ground. The other end of resistor 95 is connected to the base of transistors 63 and to one end of transistor 97. The emitter of transistor 63 and the other end of resistor 97 are connected to $-V_{cc}(B)$. The other end of resistor 99 is connected to the collector of transistor 63 and to the negative side of capacitor 69. The positive side of capacitor 69 is connected to circuit ground.

According to the operation of the power regulation circuit of FIG. 3, diode 65 provides a reference voltage ("REF") at its anode, such voltage being approximately 5.1 volts. Transistors 57, 59 provide temperature compensation so that the reference voltage stays substantially constant during the time of normal operation. The reference voltage is supplied to a basic regulator circuit that includes amplifier 53, operating as a comparator, and transistor 61, operating as a series pass element to regulate the output; i.e., transistor 61 acts as a variable resistance that drops the unregulated voltage (+$V_{cc}$(B)) down to a fixed output voltage (+5VDC) at its collector. The voltage at the collector of transistor 61 can be set at +5VDC by adjusting potentiometer 87. Thus, the collector of transistor 61 provides +$V_{cc}$(C).

Similarly, the amplifier 55 and transistor 63 act as a comparator and series pass element of a basic regulation circuit with the reference voltage as circuit ground. Thus, when regulated, the point at which resistors 91, 99 are connected together will be at approximately 0 volts referenced to ground. Because resistors 91, 99 are of equal value and have substantially the same current flowing therethrough, the voltage drop across resistor 99 will be 5 volts whereby the voltage at the collector of transistor 63 will be regulated at −5VDC. Thus −$V_{cc}$(C) is provided at the collector of transistor 63.

Referring to FIG. 4, the low battery detection circuit includes the following components:

| Component Name | Reference Number | Preferred Type or Value |
| --- | --- | --- |
| Comparator | 101 | ¼ LM 324 |
| Comparator | 103 | ¼ LM 324 |
| Inverter | 105 | 1/6 4049 |
| Diode | 107 | 1N 914 |
| Diode | 109 | 1N 914 |
| LED | 111 | 1N __ |
| Potentiometer | 113 | 40 Kohm |
| Potentiometer | 115 | 50 Kohm |
| Resistor | 117 | 10 Kohm |
| Resistor | 119 | 510 ohm |

The components of the low battery detection circuit are interconnected as follows: The reference voltage of the power regulation circuit is connected to the "+" input of comparator 101 and to one end of potentiometer 115. The other end of potentiometer 115 is connected to −$V_{cc}$(B). The arm of potentiometer 115 is connected to the "+" input of comparator 103. The "−" input of comparator 103 is connected to circuit ground. The "−" input of comparator 101 is connected to the arm of potentiometer 113. One end of potentiometer 113 is connected to +$V_{cc}$(B). The other end of potentiometer 113 is connected to circuit ground. The output of comparator 101 is connected to the cathode of diode 107. The output of comparator 103 is connected to the cathode of diode 109. The anode of diode 107 is connected to the input of inverter 105, the anode of diode 109, and one end of resistor 117. The other end of resistor 117 is connected to −$V_{cc}$(B). The output of inverter 105 is connected to one end of resistor 119. The other end of resistor 119 is connected to the anode of LED 111. The cathode of LED 111 is connected to +$V_{cc}$(A).

According to the operation of the low battery indication circuit as shown in FIG. 4, the voltage at the arm of potentiometer 113 ("V113") is a division of the potential of battery 29 with respect to ground. Thus, as the voltage of battery 29 decreases, V113 decreases proportionately thereto. Similarly, the voltage at the arm of potentiometer 115 ("V115") is a division of the difference between the reference voltage and the negative of the potential of battery 31. Thus, as long as the potential of battery 29 is slightly greater than the zener voltage of diode 65 during which time the reference voltage remains substantially constant, V115 increases as the potential of battery 31 decreases.

Comparator 101 compares V113 to the reference voltage such that the output of comparator 101 (1) will be at a logical low voltage level ("LOW") when V113 is greater than the reference voltage and (2) will be at a logical high voltage level ("HIGH") when V113 is less than the reference voltage. (As noted in the Appendix, all comparators and digital integrated circuits are connected between +$V_{cc}$(B) and −$V_{cc}$(B). Therefore, the HIGH for the preferred embodiment of the apparatus will be approximately +6VDC and the LOW for such embodiment will be approximately −6VDC.) Potentiometer 113 should be set such that when battery 29 is at full potential, i.e., about 6 volts, V113 will be substantially greater than the reference voltage and the output of comparator 101 will be LOW, but when the potential of battery 29 decreases to a particular level ("$V_{low}$"), V113 will become slightly less than the reference voltage and the output of comparator 101 will go from LOW to HIGH.

Comparator 103 compares V115 to circuit ground and its output will be LOW when V115 is less than circuit ground, i.e., when V115 is negative, and will be HIGH when V115 is greater than circuit ground, i.e., when V115 is positive. Potentiometer 115 should be set such that when battery 31 is at full potential, V115 will be negative and the output of comparator 103 will be LOW, but when the potential of battery 31 decreases below full potential to $V_{low}$, V115 will become slightly positive and the output of comparator 103 will go from LOW to HIGH.

Thus, whenever the potentials of both batteries 29, 31 are above $V_{low}$, the input of inverter 105 will be LOW, the output of inverter 105 will be HIGH and LED 111 will not be illuminated, i.e., will be "OFF". If, however, the potential of either battery decreases to $V_{low}$, the input of inverter 105 will go HIGH, the output of inverter 105 will go LOW and LED 111 will be illuminated, i.e., will be "ON". Thus, illumination of LED 111 indicates that the potential of at least one of the batteries has become equal to or less than $V_{low}$.

In the preferred embodiment, potentiometers 113, 115 are set such that $V_{low}$ is approximately 5.5 VDC. It should be apparent that other values of $V_{low}$ may be used and that $V_{low}$ for one battery may be different than that for the other battery. The value of $V_{low}$ will, however, always be greater than the reference voltage.

B. Switching circuits

As noted in the functional description of the apparatus, the characteristics of various of the functional circuits are selectably variable. In the specific component configuration of the preferred embodiment of the apparatus of the invention, such selection is accomplished through the use of mechanical switching circuits. In order to facilitate the description and illustration of the functional circuits, the configuration and operation of such switching circuits are described separately in this subsection of the description and will be referenced generally as circuits having various inputs and outputs in the descriptions of the functional circuits as a whole. Such switching circuits include (1) a latching circuit, (2) a resistor switch circuit and (3) a divider switch circuit.

1. Latching circuit

Referring to FIG. 5, the latching circuit includes the following components:

| Component Name | Reference Number | Preferred Type or Value |
|---|---|---|
| NOR R/S Latch | 121 | ¼ 4043 |
| Inverter | 123 | 1/6 4049 |
| Bilateral Switch | 125 | ¼ 4066 |
| LED | 127 | 1N — |
| Resistor | 129 | 10 Kohm |
| Resistor | 131 | 510 ohm |

The latching circuit further includes momentary, normally-open, single-pole, single-throw switch 133 having terminals 135, 137. According to the configuration of the latch circuit, terminal 135 of switch 133 and the cathode of diode 127 are connected to $+V_{cc}(A)$. Terminal 137 of switch 133 is connected to one end of resistor 129 and to the set input of latch 121. The Q output of latch 121 constitutes the LQ output of the latching circuit and is connected to the input of inverter 123 and to the control input of switch 125. The reset input of latch 121 constitutes the LR input of the latching circuit. One of the I/O terminals of switch 125 constitutes switch terminal A of the latching circuit and the other I/O terminal of switch 125 constitutes switch terminal B of the latching circuit. The output of inverter 123 is connected to one end of resistor 131. The other end of resistor 131 is connected to the anode of diode 127.

According to the operation of the latching circuit, whenever LQ is HIGH, switch 125 (the "latch switch") will be closed and LED 127 (the "latch indicator") will be on. At such time, the latching circuit is in the "on" state. Conversely, whenever LQ is LOW, the latch switch will be open and the latch indicator will be off. At such time, the latching circuit is in the "off" state. Thus, whenever switch 133 (the "control switch") is closed the latching circuit will be on regardless of the state of LR or the state of the latching circuit immediately prior to closing the control switch. If, when the control switch is released, LR is LOW, the latching circuit will remain on until, at some time after the control switch is released, LR goes HIGH, at which time the latching circuit will turn off. If, when the control switch is released, LR is HIGH, the latching circuit will immediately turn off. If, at some time while the latching circuit is off, at which time the control switch necessarily is open, LR goes LOW, the latching circuit will remain off. Thus, the latching circuit is turned on by closing the control switch and is turned off by a HIGH at LR if, at the time of such HIGH at LR, the control switch is open.

The latching circuit will hereinafter be shown as a box identified by the letter L having input LR, output LQ and switch terminals A and B.

2. Resistor switch circuit

Referring to FIG. 6, the resistor switch includes the following components:

| Component Name | Reference Number | Preferred Type or Value |
|---|---|---|
| Resistor | 139 | 1.00 Kohm |
| Resistor | 140 | 1.26 Kohm |
| Resistor | 141 | 1.58 Kohm |
| Resistor | 142 | 2.00 Kohm |
| Resistor | 143 | 2.49 Kohm |
| Resistor | 144 | 3.16 Kohm |
| Resistor | 145 | 4.02 Kohm |
| Resistor | 146 | 4.99 Kohm |
| Resistor | 147 | 6.34 Kohm |
| Resistor | 148 | 7.87 Kohm |
| Resistor | 149 | 10.0 Kohm |
| Resistor | 150 | 12.7 Kohm |
| Resistor | 151 | 15.8 Kohm |
| Resistor | 152 | 20.0 Kohm |
| Resistor | 153 | 24.9 Kohm |
| Resistor | 154 | 31.6 Kohm |

The resistor circuit further includes multi-position, rotary switch 155 having arm terminal 156 and contact terminals 157–173. One end of resistors 139–154 are connected to contact terminals 158–173, respectively. The other end of resistors 139–154 are connected together and constitute input I of the resistor switch. Contact terminal 157 of switch 155 is open. Arm terminal 156 of switch 155 constitutes output O of the resistor switch.

For the purposes of this description, the resistor switch is considered to have positions P0, when arm terminal 156 is shorted to contact terminal 157, through position P16, when arm terminal 156 is shorted to contact terminal 173. Thus, positions P1–P15 correspond to a short between arm terminal 156 and resistors 139–154, respectively. In accordance with the foregoing, when the resistor switch is in position P0, the circuit from input I to output O of the resistor switch is open. When the resistor switch is in positions P1–P16, the circuit from input I to output O of the resistor switch has a resistance corresponding to the value of resistors 139–173, respectively. Thus, the resistance from input I to output O increases as the resistor switch is moved from position P1 to position P16.

The resistor switch will hereinafter be shown as a box identified by the letter R and having input I and output O.

3. Divider switch

Referring to FIG. 7, the divider switch includes resistors 175–190, all having a value of 4.32 Kohm, resistors 191–206, all having a value of 12.7 Kohm, and multi-position rotary switch 207 having arm terminal 208 and contact terminals 209–225. One end of resistors 175–190 are connected to one end of resistors 191–206, respectively, and to contact terminals 210–225, respectively. The other end of resistors 175–190 are connected to terminals 209–224, respectively. The other ends of resistors 191–206 are all connected to circuit ground. Contact terminal 209 constitutes input I of the divider switch and arm terminal 208 constitutes output O of the divider switch.

For the purposes of this description, the divider switch is considered to have positions P0–P16 corresponding to a short between arm terminal 208 and contact terminals 209–225, respectively. Thus, when the divider switch is in position P0, there is a short between input I and output O of the divider switch whereby the voltage at input I (VI) will be the same as that at output O (VO). When the divider switch is in positions P1–P16, VO will be a division of VI. The approximate relation of VO to VI will be as follows:

| Position | Relation (VO/VI) |
|---|---|
| P1 | $7.46 \times 10^{-1}$ |

-continued

| Position | Relation (VO/VI) |
|---|---|
| P2 | $5.57 \times 10^{-1}$ |
| P3 | $4.15 \times 10^{-1}$ |
| P4 | $3.10 \times 10^{-1}$ |
| P5 | $2.31 \times 10^{-1}$ |
| P6 | $1.73 \times 10^{-1}$ |
| P7 | $1.29 \times 10^{-1}$ |
| P8 | $9.61 \times 10^{-2}$ |
| P9 | $7.17 \times 10^{-2}$ |
| P10 | $5.35 \times 10^{-2}$ |
| P11 | $3.99 \times 10^{-2}$ |
| P12 | $2.98 \times 10^{-2}$ |
| P13 | $2.22 \times 10^{-2}$ |
| P14 | $1.66 \times 10^{-2}$ |
| P15 | $1.24 \times 10^{-2}$ |

The divider switch will hereinafter be shown as a box identified by the letter D and having input I and output O.

C. Signal generation circuit

Referring to FIG. 8, signal generation circuit 11 of the preferred embodiment of the invention includes the following components:

| Component Name | Reference Number | Preferred Type or Value |
|---|---|---|
| Signal Generator | 227 | 8038 |
| Timer | 229 | LM555 |
| Bilateral Switch | 231 | ¼ 4066 |
| Comparator | 233 | ¼ LM324 |
| Diode | 235 | 1N914 |
| Diode | 237 | 1N914 |
| Capacitor | 239 | 0.1 mfd. |
| Capacitor | 241 | 0.001 mfd. |
| Capacitor | 243 | 0.001 mfd. |
| Capacitor | 245 | 0.01 mfd. |
| Potentiometer | 247 | 2 Kohm |
| Potentiometer | 249 | 2 Kohm |
| Potentiometer | 251 | 10 Kohm |
| Potentiometer | 253 | 2 Kohm |
| Resistor | 255 | 100 Kohm |
| Resistor | 257 | 100 Kohm |
| Resistor | 259 | 75 Kohm |
| Resistor | 261 | 47 Kohm |
| Resistor | 263 | 9.1 Kohm |
| Resistor | 265 | 2.0 Kohm |
| Resistor | 267 | — |
| Resistor | 269 | — |
| Resistor | 271 | 56 Kohm |
| Resistor | 273 | 10 Kohm |
| Resistor | 275 | 10 Kohm |
| Resistor | 277 | 10 Kohm |
| Resistor | 279 | 10 Kohm |
| Resistor | 281 | 100 Kohm |
| Resistor | 283 | 100 Kohm |
| NOR S/R Latch | 285 | ¼ 4043 |
| NOR S/R Latch | 287 | ¼ 4043 |

Signal generation circuit 11 further includes latching circuits 289, 291.

The components of signal generation circuit 11 of FIG. 8 are connected as follows: one end terminal of potentiometer 247, the arm terminal of potentiometer 247, one end terminal of potentiometer 249 and the arm terminal of potentiometer 249 are all connected to $+V_{cc}(C)$. The other end terminals of potentiometers 247, 249 are connected to one end of resistors 263, 265, respectively. The other ends of resistors 263, 265 are connected to switch terminals A of latching circuits 289, 291, respectively. Outputs LQ of latching circuits 289, 291 are connected to one end of resistors 255, 257, respectively. The other ends of resistors 255, 257 are both connected to the "+" terminal of comparator 233. The S (set) inputs of latches 285, 287 are connected to one end of resistors 277, 279, respectively. The other ends of resistors 277, 279 are connected to $-V_{cc}(B)$. The Q outputs of latches 285, 287 are connected to one end of resistors 281, 283, respectively. The other ends of resistors 281, 283 are connected to the "+" inputs of comparator 233. The "−" input of comparator 233 is connected to one end of resistor 259 and to one end of resistor 261. The other end of resistor 259 is connected to $+V_{cc}(B)$. The other end of resistor 261 is connected to $-V_{cc}(B)$. The output of comparator 233 is connected to the LR inputs of latching circuits 289, 291 and to the R (reset) inputs of latches 285, 287. The B switch terminals of latching circuits 289, 291 are both connected to the arm terminal of potentiometer 251. The end terminals of potentiometer 251 are connected between the DC/FC inputs of generator 227. The FM BIAS output of generator 227 is connected to the FM INPUT of generator 227. The CT control of generator 227 is connected to one side of capacitor 239. The SGN ADJ control of generator 227 is connected to one end of resistor 271. The other side of capacitor 239 and the other end of resistor 271 are connected to $-V_{cc}(C)$. The SQ (square wave) output of generator 227 is connected to one end of resistor 273 and to one side of capacitor 241. The other side of capacitor 241 is connected to one end of resistor 275, to the anode of diode 237, to the cathode of diode 235 and to the TR (trigger) input of timer 229. The other end of resistor 273, the other end of resistor 275 and the anode of diode 235 are all connected to $+V_{cc}(C)$. The cathode of diode 237 is connected to circuit ground. The TH (threshold) control of timer 229 is connected to the DIS (discharge) control of timer 229, to one side of capacitor 243, to one I/O terminal of switch 231 and to one end of resistor 269. The other I/O terminal of switch 231 is connected to one end of resistor 267. The other end of resistor 267 is connected to one end terminal of potentiometer 253. The other end terminal of potentiometer 253 is connected to the arm terminal of potentiometer 253, to one end of resistor 269 and to $+V_{cc}(C)$. The control input of switch 231 is connected to the LQ output of latching circuit 291. The R (reset) input of timer 229 is connected to $+V_{cc}(C)$. The CONT (control) input of timer 229 is connected to one side of capacitor 245. The other sides of capacitors 243, 245 are connected to circuit ground. The output of timer 229 constitutes output $O_{SG}$ of signal generation circuit 11.

According to the operation of the FIG. 8 embodiment of signal generation circuit 11, signal generator 227 produces a signal at SQ that varies in accordance with the setting of potentiometer 251 and the resistance between the arm terminal of potentiometer 251 and $+V_{cc}(C)$ the "frequency control resistance"). When the frequency control resistance is infinite, the signal at SQ will be dc with a level of about 0 volts. When the frequency control resistance is less than infinite, the SQ signal will be a square wave having upper and lower voltage levels of approximately $+V_{cc}(C)$, $-V_{cc}(C)$, respectively. The proportion of the total period that the signal at output SQ of generator 227 is at the high level or the low level depends on the setting of potentiometer 251. In the preferred embodiment, potentiometer 251 is set so that the waveform of the signal at output SQ is symmetrical.

The frequency of the square wave is dependent on the value of the frequency control resistance. In the preferred embodiment, the frequency control resistance may be discretely varied between a first resistance (FCR1) and a second resistance (FCR2). The values of FCR1, FCR2 are equal to the resistances between the A terminals of latching circuits 289, 291, respectively, and the arm terminals of potentiometers 247, 249, respectively, and may be varied by adjusting such potentiometers. In the preferred embodiment, potentiometer 247 is set such that when FCR1 is the frequency control resistance, the frequency of the signal at SQ is 125 Hz, and potentiometer 249 is set such that when FCR2 is the frequency control resistance, the frequency of the signal at SQ is 250 Hz.

FCR1 will be the frequency control resistance when the latch switch of latching circuit 289 is closed, i.e., when latching circuit 289 is on, and FCR2 will be the frequency control resistance when the latch switch of latching circuit 291 is closed, i.e., when latching circuit 291 is on. Latching circuits 289, 291 are connected to comparator 233 such that momentary closure of the control switch of one of latching circuits 289, 291 will cause such latching circuit to turn on while turning the other of latching circuits 289, 291 off. Such one latching circuit will then remain on until the control switch of the other latching circuit is at least momentarily closed.

Such operation occurs as follows: the voltage at the "−" input of comparator 233 is always approximately:

$$-V_{cc}(B)+0.385(+V_{cc}(B)-(-V_{cc}(B)))$$

The voltage at the "+" input of comparator 233 will depend on the state of the LQ outputs of latching circuits 289, 291. In this regard, it should be noted that the voltage at an LQ output that is HIGH will be approximately $+V_{cc}(B)$, and the voltage at an LQ output that is LOW will be approximately $-V_{cc}(B)$. The Q outputs of latches 285, 287 will always be LOW and, therefore, will always be at approximately $-V_{cc}(B)$. Thus, if latching circuits 289, 291 are both off, the voltage at the "+" input of comparator 233 will be approximately $-V_{cc}(B)$ which is less than the voltage at the "−" input of comparator 233; if only one of the latching circuits 289, 291 is on, the voltage at the "+" input of comparator 233 will be approximately:

$$-V_{cc}(B)+0.248(+V_{cc}(B)-(-V_{cc}(B)))$$

which is less than the voltage at the "−" input; and if both of latching circuits 289, 291 are on, the voltage at the "+" input of comparator 233 will be approximately:

$$-V_{cc}(B)+0.500(+V_{cc}(B)-(-V_{cc}(B)))$$

which is greater than the voltage at the "−" input of comparator 233. As a result, the output of comparator 233 and the LR inputs of latching circuits 289, 291 will be HIGH when both of latching circuits 289, 291 are on and will be LOW at all other times.

In accordance with the foregoing, if neither of latching circuits 289, 291 is on, the LR inputs of both latching circuits will be LOW. Because neither latching circuit is on, the frequency control resistance will be infinite and the signal at SQ will be approximately 0 VDC. If the control switch of a first of latching circuits 289, 291 is then closed at least momentarily (several milliseconds), then the latch switch of such first latching circuit will close and the LQ output of such first latching circuit will go HIGH. Because only one of latching circuits 289, 291 will be on, the LR inputs of both latching circuits will be LOW. Thus, in accordance with the description of the latching circuit, supra, such first latching circuit will remain on even after the control switch of such latching circuit is released. If the control switch of the second of latching circuits 289, 291 is then closed at least momentarily, the latch switch of such second latching circuit will close and the LQ output of such second latching circuit will go HIGH. As a result, the LQ output of both of latching circuits will be HIGH and the LR inputs of latching circuits will both go HIGH. Because the LR inputs will go HIGH only a few microseconds after the control switch of the second latching circuit is closed, such control switch will still be closed when LR goes HIGH whereby such second latching circuit will remain on. The control switch of the first latching circuit, however, will be open when LR goes HIGH whereby such first latching circuit will turn off. As a result, immediately after LR goes HIGH, the LQ output of only one of the latching circuits will be HIGH whereby LR will again go LOW. Thus, by the time the control switch of the second latching circuit is released, LR will be LOW and such second latching circuit will remain on until the control switch of the first latching circuit is at least momentarily closed at which time the first latching circuit will turn on and the second latching circuit will turn off.

Because the latch indicator of a latching circuit is on when the latch switch of such latching circuit is closed, the latch indicators of latching circuits 289, 291 provide a visible indication that the frequency of the signal at SQ is 125 Hz, 250 Hz, respectively.

The signal at SQ is supplied to the filter comprising resistors 273, 275 and capacitor 241 where the dc component, if any, of such signal is removed. Such signal is then clipped by diodes 235, 237 so as to produce a symmetrical square wave signal with an upper level of approximately $+V_{cc}(C)$ and a lower level at about 0 volts. This clipped signal is applied to the trigger input of timer 229 which will provide a positive-going pulse at $O_{SG}$ on every negative-going transition of the clipped signal. Thus, the signal at $O_{SG}$ will include a continuous train of positive-going pulses produced at the frequency of the signal at output SQ of generator 227, i.e., either 125 Hz or 250 Hz.

The width of the pulses at $O_{SG}$ depends on the state of switch 231 and, when switch 231 is closed, on the setting of potentiometer 253. Switch 231 will be closed when latching circuit 291 is on and will be open when latching circuit 291 is off. Thus, in the preferred embodiment, switch 231 will be closed when the frequency of the pulses at $O_{SG}$ is 250 Hz and will be open when such frequency is 125 Hz. In the preferred embodiment, potentiometer 253 is set such that the rms value of the signal at $O_{SG}$ with respect to ground when switch 231 is open is the same as such rms value when switch 231 is closed. Because the energy of a signal is directly related to the rms value of the signal, such a setting causes the energy of the signal at $O_{SG}$ to be constant regardless of the frequency of the pulses at $O_{SG}$.

In accordance with the foregoing, signal generation circuit 11 of the preferred embodiment produces at $O_{SG}$ a constant energy signal comprising a train of narrow positive-going pulses, the frequency of such pulses selectable as either 125 Hz or 250 Hz. A visible indication of the frequency is provided by the latch indicators of latching circuits 289, 291; i.e., when the latch indicator of latching circuit 289 is on, the frequency is 125 Hz, and when the latch indicator of latching circuit 291 is on, the frequency is 250 Hz. Such frequency is quickly changed between 125 Hz and 250 Hz by momentary closure of the control switches of latching circuits 289, 291.

D. Formant filter circuits

Although some capacitances and resistances vary between formant filter circuits 13 and 15, the component configurations of such formant filter circuits are largely identical and, therefore, filter circuits 13, 15 will be described together. Formant filter circuit 17 includes some additional differences and will be described separately.

(1) Formant filter circuits 13, 15

Referring to FIG. 9, formant filter circuits 13, 15 of the preferred embodiment include operational amplifier circuit 293 and feedback resistance control circuit 295.

As shown in FIG. 9, operational amplifier circuit 293 includes the following components (where component values vary between circuits 13 and 15, the value for each circuit is separately indicated):

| Component Name | Reference Numbers | Preferred Type or Value |
|---|---|---|
| Operational Amplifier | 297 | ½ 747 |
| Operational Amplifier | 299 | ½ 747 |
| Operational Amplifier | 301 | 741 |
| Capacitor | 303 | 0.015 mfd. (Circuit 13) |
|  |  | .0068 mfd. (Circuit 15) |
| Capacitor | 305 | 0.015 mfd. (Circuit 13) |
|  |  | .0068 mfd. (Circuit 15) |
| Potentiometer | 307 | — |
| Resistor | 309 | 10 Kohm (Circuit 13) |
|  |  | 14 Kohm (Circuit 15) |
| Resistor | 311 | 220 Kohm (Circuit 13) |
|  |  | 360 Kohm (Circuit 15) |
| Resistor | 313 | 10 Kohm |
| Resistor | 315 | 10 Kohm |
| Resistor | 317 | 7.5 Kohm (Circuit 13) |
|  |  | 8.2 Kohm (Circuit 15) |

The components of operational amplifier circuit 293 are connected as follows: one end terminal of potentiometer 307 constitutes input $I_{FF1,2}$ of the formant filter circuit and, for both formant filter circuits 13, 15, is connected to output $O_{SG}$ of signal generation circuit 11. The other end terminal of potentiometer 307 is connected to the arm terminal of potentiometer 307 and to one end of resistor 309. The other end of resistor 309 is connected to one side of capacitor 303, to one end of resistor 311 and to the inverting input of amplifier 297. The output of amplifier 297 constitutes output $O_{FF1,2}$ of the formant filter circuit and is connected to the other side of capacitor 303, to the other end of resistor 311 and to one end of resistor 313. The other end of resistor 313 is connected to one end of resistor 315 and to the inverting input of amplifier 299. The output of amplifier 299 is connected to the other end of resistor 315 and to one end of resistor 317. The other end of resistor 317 is connected to one side of capacitor 305 and to the inverting input of amplifier 301. The output of amplifier 301 is connected to the other side of capacitor 305. The non-inverting inputs of amplifiers 297, 299, 301 are all connected to circuit ground.

When a resistance is connected between the output of amplifier 301 and the inverting input of amplifier 297, operational amplifier circuit 293 operates as a second-order, active bandpass filter known in the art of active-filter design as a biquadratic filter. With the component values set forth above, the bandwidth of the biquadratic filter of filter circuits 13, 15, will be 50 Hz, 75 Hz, respectively. The center frequencies of such filters will vary according to the resistance between the output of amplifier 301 and the inverting input of amplifier 297 (the "feedback resistance").

The feedback resistance may be set at any one of eight values Fr1–FR8 by means of feedback resistance control circuit 295. As shown in FIG. 9, feedback resistance control circuit 295 includes the following components:

| Component Name | Reference Numbers | Preferred Type or Value |
|---|---|---|
| Comparator | 319 | LM324 |
| Resistor | 321 | 10 Kohm |
| Resistor | 322 | 10 Kohm |
| Resistor | 323 | 10 Kohm |
| Resistor | 324 | 10 Kohm |
| Resistor | 325 | 10 Kohm |
| Resistor | 326 | 10 Kohm |
| Resistor | 327 | 10 Kohm |
| Resistor | 328 | 10 Kohm |
| Resistor | 329 | 75 Kohm |
| Resistor | 330 | 18 Kohm |
| Resistor | 331 | 240 Kohm (Circuit 13) |
|  |  | 75 Kohm (Circuit 15) |
| Resistor | 332 | 110 Kohm (Circuit 13) |
|  |  | 62 Kohm (Circuit 15) |
| Resistor | 333 | 62 Kohm (Circuit 13) |
|  |  | 39 Kohm (Circuit 15) |
| Resistor | 334 | 39 Kohm (Circuit 13) |
|  |  | 27 Kohm (Circuit 15) |
| Resistor | 335 | 27 Kohm (Circuit 13) |
|  |  | 20 Kohm (Circuit 15) |
| Resistor | 336 | 20 Kohm (Circuit 13) |
|  |  | 15 Kohm (Circuit 15) |
| Resistor | 337 | 15 Kohm (Circuit 13) |
|  |  | 11 Kohm (Circuit 15) |
| Resistor | 339 | 9.1 Kohm |
| Potentiometer | 340 | 10 Kohm |
| Potentiometer | 341 | 10 Kohm |
| Potentiometer | 342 | 10 Kohm |
| Potentiometer | 343 | 10 Kohm (Circuit 13) |
|  |  | 2 Kohm (Circuit 15) |
| Potentiometer | 344 | 2 Kohm |
| Potentiometer | 345 | 2 Kohm |
| Potentiometer | 346 | 2 Kohm |
| Potentiometer | 347 | 2 Kohm |

Feedback resistance control circuit 295 further includes latching circuits 348–355.

The components of feedback resistance control circuit 295 are connected as follows: one end terminal and the arm terminal of each of potentiometers 340–347 are connected to the output of amplifier 301. The other end terminal of potentiometers 340–347 is connected to one end of resistors 331–339, respectively. The other end of resistors 331–339 are connected to the B terminals of latching circuits 348–355, respectively. The A terminals of latching circuits 348–355 are all connected to the inverting input of amplifier 297. The LQ outputs of latching circuits 348–355 are connected to one end of resistors 321–328, respectively. The other ends of resistors 321–328 are all connected to the "+" input of comparator 319. The "−" input of comparator 319 is connected to one end of resistor 329 and to one end of resistor 330. The other end of resistor 329 is connected to $+V_{cc}(B)$. The other end of resistor 330 is connected to $-V_{cc}(B)$. The LR inputs of latching circuits 348–355 are connected to the output of comparator 319.

In accordance with the configuration of feedback resistance control circuit 295, FR1–FR8 comprise the series combinations of resistors 331–339, respectively, and potentiometers 340–347, respectively. Thus, the resistive values of FR1–FR8 can be continuously varied over the range of potentiometers 340–347, respectively, by adjusting such potentiometers.

Selection of the feedback resistance is accomplished in substantially the same manner as selection of the frequency control resistance of signal generation circuit 11 as described, supra. Thus, FR1 will be the feedback resistance when the latch switch of latching circuit 348 is closed, FR2 will be the feedback resistance when the latch switch of latching circuit 349 is closed, FR3 will be the feedback resistance when the latch switch of latching circuit 350 is closed, FR4 will be the feedback resistance when the latch switch of latching circuit 351 is closed, FR5 will be the feedback resistance when the latch switch of latching circuit 352 is closed, FR6 will be the feedback resistance when the latch switch of latching circuit 353 is closed, FR7 will be the feedback resistance when the latch switch of latching circuit 354 is closed, and FR8 will be the feedback resistance when the latch switch of latching circuit 355 is closed. Latching circuits 348–355 are connected to comparator 319 such that momentary closure of the control switch of one of latching circuits 348–355 will cause such latching circuit to turn on while turning all other of latching circuits 348–355 off. Such one latching circuit will then remain on until the control switch of one of the other latching circuits is at least momentarily closed.

In this regard, it will be noted that the voltage at the "−" input of comparator 319 is always approximately:

$$-V_{cc}(B) + 0.194(+V_{cc}(B) - (-V_{cc}(B)))$$

If latching circuits 348–355 are all off, the voltage at the "+" input of comparator 319 will be approximately $-V_{cc}(B)$ which is less than the voltage at the "−" input of comparator 233; if only one of latching circuits 348–355 is on, the voltage at the "+" input of comparator 233 will be approximately:

$$-V_{cc}(B) + 0.125(+V_{cc}(B) - (-V_{cc}(B)))$$

which is less than the voltage at the "−" input; and if two or more of latching circuits 348–355 are on, the voltage at the "+" input of comparator 233 will be approximately equal to or greater than:

$$-V_{cc}(B) + 0.250(+V_{cc}(B) - (-V_{cc}(B)))$$

which is greater than the voltage at the "−" input of comparator 233. As a result, the output of comparator 233 and the LR inputs of latching circuits 348–355 will be HIGH when two or more of latching circuits 348–355 are on and will be LOW at all other times. Thus, if all of latching circuits 348–355 are off, any one of latching circuits 348–355 can be turned on by at least momentarily closing the control switch of such latching circuit. If one of latching circuits 348–355 is on, a different latching circuit can be turned on by momentarily closing the control switch of such different latching circuit. Such momentary closure of the control switch of such different latching circuit will produce a positive-going pulse at the output of comparator 319 thus resetting the latching circuit previously on. Because, in most instances, the control switch of such different latching circuit will still be closed at the time of such positive-going pulse, such different latching circuit will remain on after the control switch is released.

Therefore, by momentarily closing the control switch of latching circuits 348–355, the feedback resistance can be set at FR1–FR8, respectively, whereby the center frequency of the formant filter circuit can be selectively varied. In the preferred embodiment of formant filter circuit 13, potentiometers 340–347 are set such that when the feedback resistance of formant filter circuit 13 is a particular FR, the center frequency of formant filter circuit 13 will be as follows:

| FR | Frequency | FR | Frequency |
|----|-----------|----|-----------|
| 1  | 250 Hz    | 5  | 750 Hz    |
| 2  | 375 Hz    | 6  | 875 Hz    |
| 3  | 500 Hz    | 7  | 1000 Hz   |
| 4  | 625 Hz    | 8  | 1250 Hz   |

Furthermore, in the preferred embodiment, potentiometers 340–347 of formant filter circuit 15 are set such that when the feedback resistance of formant filter circuit 15 is a particular FR, the center frequency of formant filter circuit 15 will be as follows:

| FR | Frequency | FR | Frequency |
|----|-----------|----|-----------|
| 1  | 875 Hz    | 5  | 1750 Hz   |
| 2  | 1000 Hz   | 6  | 2000 Hz   |
| 3  | 1250 Hz   | 7  | 2250 Hz   |
| 4  | 1500 Hz   | 8  | 2500 Hz   |

Some of the center frequencies of formant filter circuits 13, 15 of the preferred embodiment as set forth in the preceding tables, specifically, 375 Hz, 625 Hz and 875 Hz, are not harmonics of one of the fundamental frequencies selectable in signal generation circuit 11 of the preferred embodiment, specifically, 250 Hz. Therefore, whenever 250 Hz is selected as the fundamental frequency, a selection of FR2, FR4 or FR6 as the center frequency of formant filter circuit 13 or a selection of FR1 as the center frequency of formant filter circuit 15 will produce undesirable results. As a result, the preferred embodiment of the invention includes an illegal combination detector circuit that provides an indication whenever such an undesirable selection is made. The illegal combination detector circuit is described infra in the next section.

(2) Formant filter circuit 17

Referring to FIG. 10, formant filter 17 of the preferred embodiment includes operational amplifier circuit 357 and feedback resistance control circuit 359.

As shown in FIG. 10, operational amplifier circuit 375 includes the following components:

| Component Name | Reference Number | Preferred Type or Value |
|----------------|------------------|-------------------------|
| Operational Amplifier | 361 | ½ 747 |
| Operational Amplifier | 363 | ½ 747 |
| Operational Amplifier | 365 | 741 |
| Capacitor | 367 | 0.0039 mfd. |
| Capacitor | 369 | 0.0039 mfd. |
| Potentiometer | 371 | — |
| Resistor | 373 | 18 Kohm |
| Resistor | 375 | 390 Kohm |
| Resistor | 377 | 10 Kohm |
| Resistor | 379 | 10 Kohm |
| Resistor | 381 | 12 Kohm |

The components of operational amplifier circuit 357 are connected as follows: one end terminal of potentiometer 371 constitutes input $I_{FF3}$ of formant filter circuit 17 and is connected to output $O_{SG}$ of signal generation circuit 11. The other end terminal of potentiometer 371 is connected to the arm terminal of potentiometer 371 and to one end of resistor 373. The other end of resistor 373 is connected to one side of capacitor 367, to one end of resistor 375 and to the inverting input of amplifier 361. The output of amplifier 361 constitutes output $O_{FF3}$ of formant filter circuit 17 and is connected to the other side of capacitor 367, to the other end of resistor 375 and to one end of resistor 377. The other end of resistor 377 is connected to one end of resistor 379 and to the inverting input of amplifier 363. The output of amplifier 363 is connected to the other end of resistor 379 and to one end of resistor 381. The other end of resistor 381 is connected to one side of capacitor 369 and to the inverting input of amplifier 365. The output of amplifier 365 is connected to the other side of capacitor 369. The non-inverting inputs of amplifiers 361, 363, 365 are all connected to circuit ground.

When a resistance is connected between the output of amplifier 365 and the inverting input of amplifier 361, operational amplifier circuit 357 operates as a biquadratic filter. With the component values set forth above, the band width of the biquadratic filter of filter circuit 17 will be 100 Hz. The center frequency of the biquadratic filter of filter circuit 17 will vary according to the resistance between the output of amplifier 365 and the inverting input of amplifier 361 (the "feedback resistance").

The feedback resistance may be set at any one of six values FR9–FR14 by means of feedback resistance control circuit 359. As shown in FIG. 10, feedback resistance control circuit 359 includes the following components:

| Component Name | Reference Number | Preferred Type or Value |
| --- | --- | --- |
| Comparator | 383 | LM324 |
| NOR S/R Latch | 385 | ¼ 4043 |
| NOR S/R Latch | 387 | ¼ 4043 |
| Potentiometer | 389 | 2 Kohm |
| Potentiometer | 390 | 2 Kohm |
| Potentiometer | 391 | 2 Kohm |
| Potentiometer | 392 | 2 Kohm |
| Potentiometer | 393 | 2 Kohm |
| Potentiometer | 394 | 2 Kohm |
| Resistor | 395 | 39 Kohm |
| Resistor | 396 | 30 Kohm |
| Resistor | 397 | 24 Kohm |
| Resistor | 398 | 16 Kohm |
| Resistor | 399 | 12 Kohm |
| Resistor | 400 | 9.1 Kohm |
| Resistor | 401 | 100 Kohm |
| Resistor | 402 | 100 Kohm |
| Resistor | 403 | 100 Kohm |
| Resistor | 404 | 100 Kohm |
| Resistor | 405 | 100 Kohm |
| Resistor | 406 | 100 Kohm |
| Resistor | 407 | 10 Kohm |
| Resistor | 408 | 100 Kohm |
| Resistor | 409 | 10 Kohm |
| Resistor | 410 | 100 Kohm |
| Resistor | 411 | 75 Kohm |
| Resistor | 412 | 18 Kohm |

Feedback resistance control circuit 369 further includes latching circuits 413–418.

The components of feedback resistance control circuit 359 are connected as follows: one end terminal and the arm terminal of each of potentiometers 389–394 are connected to the output of amplifier 365. The other end terminal of potentiometers 389–394 are connected to one end of resistors 395–400, respectively. The other end of resistors 395–400 are connected to the B terminals of latching circuits 413–418, respectively. The A terminals of latching circuits 413–418 are all connected to the inverting input of amplifier 361. The LQ outputs of latching circuits 413–418, are connected to one end of resistors 401–406, respectively. The other end of resistors 401–406 are all connected to the "+" input of comparator 383. The "−" input of comparator 383 is connected to one end of resistor 311 and to one end of resistor 412. The other end of resistor 411 is connected to $+V_{cc}(B)$. The other end of resistor 412 is connected to $-V_{cc}(B)$. The output of comparator 383 is connected to the LR inputs of each of latching circuits 413–418 and to the reset ("R") inputs of latches 385, 387. The Q outputs of latches 385, 387 are connected to one end of resistors 408, 410, respectively. The other end of resistors 408, 410 are connected to the "+" input of comparator 383. The set ("S") inputs of latches 385, 387 are connected to one end of resistors 407, 409, respectively. The other end of resistors 407, 409 are connected to $-V_{cc}(B)$.

In accordance with the configuration of feedback resistance control circuit 359, FR9–FR14 comprise the series combinations of resistors 395–400, respectively, and potentiometers 389–394, respectively. Thus, the resistive values of FR9–FR14 can be continuously varied over the range of potentiometers 389–394 (i.e., 2Kohm), respectively, by adjusting such potentiometers.

Selection of the feedback resistance is accomplished in substantially the same manner as selection of the frequency control rresistance of signal generation circuit 11 as described supra. Thus, FR9 will be the feedback resistance when the latch switch of latching circuit 413 is closed, FR10 will be the feedback resistance when the latch switch of latching circuit 414 is closed, FR11 will be the feedback resistance when the latch switch of latching circuit 415 is closed, FR12 will be the feedback resistance when the latch switch of latching circuit 416 is closed, FR13 will be the feedback resistance when the latch switch of latching circuit 417 is closed and FR14 will be the feedback resistance when the latch switch of latching circuit 418 is closed. Latching circuits 413, 418 are connected to comparator 383 such that momentary closure of the control switch of one of the latching circuits 413–418 will cause such latching circuit to turn on while turning all other of latching circuits 413–418 off. Such one latching circuit will then remain on until the control switch of one of the other latching circuits is at least momentarily closed.

In this regard, it will be noted that the voltage at the "−" input of comparator 383 is always approximately:

$$-V_{cc}(B) + 0.194(+V_{cc}(B) - (-V_{cc}(B)))$$

If latching circuits 413, 418 are all off, the voltage at the "+" input of comparator 383 will be approximately $-V_{cc}(B)$ which is less than the voltage at the "−" input of comparator 383; if only one of the latching circuits 413, 418 is on, the voltage at the "+" input of comparator will be approximately:

$$-V_{cc}(B) + 0.125(+V_{cc}(B) - (-V_{cc}(B)))$$

which is less than the voltage at the "−" input; and if two or more of latching circuits 413–418 are on, the voltage at the "+" input of comparator 383 will be approximately equal to or greater than:

$$-V_{cc}(B) + 0.250(+V_{cc}(B) - (-V_{cc}(B)))$$

which is greater than the voltage at the "−" input of comparator 233. As a result, the output of comparator 383 and the LR inputs of latching circuits 413–418 will be HIGH when two or more of latching circuits 413–418 are on and will be LOW at all other times. Thus, if all of latching circuits 413–418 are off, any one of latching circuits 413–418 can be turned on by at least momentarily closing the control switch of such latching circuit. If one of latching circuits 413–418 is on, a different latching circuit can be turned on by momentarily closing the control switch of such different latching circuit. Such momentary closure of the control switch of such different latching circuit will produce a positive-going pulse of the output of comparator 383 thus resetting the latching circuit previously on. Because, in most instances, the control switch of such different latching circuit will still be closed at the time of such positive-going pulse, such different latching circuit will remain on after the control switch is released.

Therefore, by momentarily closing the control switch of latching circuit 413–418, the feedback resistance of amplifier circuit 357 can be set at FR9–FR14, respectively, whereby the center frequency of formant filter circuit 17 can be selectively varied. In the preferred embodiment of formant filter circuit 17, potentiometers 389–394 are set so that when the feedback resistance of formant filter circuit 17 is a particular FR, the center frequency of formant filter circuit 17 will be as follows:

| FR | Frequency | FR | Frequency |
| --- | --- | --- | --- |
| 9 | 2000 Hz | 12 | 3000 Hz |
| 10 | 2250 Hz | 13 | 3500 Hz |
| 11 | 2500 Hz | 14 | 4000 Hz |

E. Illegal Combination Detection Circuit

Referring to FIG. 11, the illegal combination detector circuit of the preferred embodiment includes the following components:

| Component Name | Reference Number | Preferred Type or Value |
| --- | --- | --- |
| 2-Input NAND Gate | 421 | ¼ 4011 |
| 2-Input NAND Gate | 422 | ¼ 4011 |
| 2-Input NAND Gate | 423 | ¼ 4011 |
| 2-Input NAND Gate | 424 | ¼ 4011 |
| 8-Input NAND Gate | 425 | 4068 |
| Inverter | 426 | 1/6 4049 |
| Resistor | 427 | 510 Ohm |
| LED | 428 | 1N — |

The components of the illegal combination detector circuit of the preferred embodiment are connected as follows: one input of each of gates 421–424 is connected to the LQ output of latching circuit 291 of signal generation circuit 11. The other input of gates 421–423 is connected to the LQ outputs of latching circuits 349, 351, 352, respectively, of formant filter circuit 13. The other input of gate 424 is connected to the LQ output of latching circuit 348 of formant filter circuit 15. The outputs of gates 421–424 are all connected to a separate input of gate 425. The remaining inputs of gate 425 are connected to circuit ground. The output of gate 425 is connected to the input of inverter 426 and the output of inverter 426 is connected to one end of resistor 427. The other end of resistor 427 is connected to the anode of LED 428 and the cathode of LED 428 is connected to $+V_{cc}(A)$.

In accordance with the configuration of the illegal combination detector circuit of the preferred embodiment, LED 428 will be on whenever the output of one of gates 421–424 is LOW. Thus, LED 428 will be on whenever the LQ output of latching circuit 291 of signal generation circuit 11 is HIGH, i.e., whenever the fundamental frequency is 250 Hz, and the LQ output of one of latching circuits 349, 351, 353 of formant filter circuit 13 and 348 of formant filter circuit 15 is HIGH, i.e., whenever the center frequency selected for formant filter circuit 13 is 375 Hz, 625 Hz, or 875 Hz or the center frequency of formant filter circuit 15 is 875 Hz.

F. Mixing Circuit

Referring to FIG. 12, mixing circuit 19 of the preferred embodiment includes the following components:

| Component Name | Reference Number | Preferred Type or Value |
| --- | --- | --- |
| Operational Amplifier | 431 | 741 |
| Potentiometer | 433 | 2 Kohm |
| Resistor | 435 | — |

Mixing circuit 19 of the preferred embodiment further includes resistor switch circuits 437, 438, 439.

The components of mixing circuit 19 of the preferred embodiment are connected as follows: input I of resistor switch circuit 437 is connected to output $O_{FF1,2}$ of formant filter circuit 13, output I of resistor switch circuit 438 is connected to output $O_{FF1,2}$ of formant filter circuit 15 and output I of resistor switch circuit 439 is connected to output $O_{FF3}$ of formant filter circuit 17. Outputs O of resistor switch circuits 437–439 are all connected to one end of resistor 435 and to the inverting input of amplifier 431. The other end of resistor 435 is connected to one end terminal of potentiometer 433. The output of amplifier 431 constitutes output $O_M$ of mixing circuit 19 and is connected to the other end terminal of potentiometer 433 and to the arm terminal of potentiometer 433. The non-inverting input of amplifier 431 is connected to circuit ground.

In order to facilitate the description of the operation of mixing circuit 19 of the preferred embodiment, it will be understood that R437, R438, R439 are the resistances between input I and output O of resistor switch circuits 437, 438, 439, respectively, such resistances being variable in accordance with the description of the resistor switch circuit, supra. RFM will be used to designate the feedback resistance of amplifier 431, i.e., the resistance between the output and the inverting input of amplifier 431. Thus RFM will be variable over a range equal to the value of potentiometer 433. Also, the signals at input I of resistor switch circuits 437, 438, 439 will be referred to as V437, V438, V439, respectively.

Amplifier 431 operates as a scaling adder that applies a gain to V437, V438, V439 and adds such signals together to provide a signal $V_{OM}$ at output $O_M$ that is equal to the inverse of the scaled algebraic sum of V437, V438, V439. The gain applied to V437, V438, V439 is equal to RFM divided by R437, R438, R439, respectively. Thus, $$V_{OM} = -\frac{RFM}{R437} V437 + \frac{RFM}{R438} V438 + \frac{RFM}{R439} V439$$

In this regard, it should be apparent that if the switch of one of resistor switch circuits 437, 438, 439 is in position P$\phi$, the resistance of such resistor switch circuit will be infinite, the gain applied to the signal at input I of such resistor switch circuit will be zero and the signal at input I of such resistor switch circuit will not be added into $V_{OM}$. Furthermore, when the switch of one of resistor switch circuits 437, 438, 439 is moved from position P1 to position P16, the gain applied to the signal at input I of such resistance switch circuit will be decreased. Specifically, if potentiometer 433 is set such that RFM equals 1Kohm, the gain applied to the signal at input I of one of resistor switch circuits 437, 438, 439 for each of positions P1–P16 of the switch of such circuit will be:

| Position | Gain | Position | Gain |
|---|---|---|---|
| P1 | 0 db | P9 | −16 db |
| P2 | −2 db | P10 | −18 db |
| P3 | −4 db | P11 | −20 db |
| P4 | −6 db | P12 | −22 db |
| P5 | −8 db | P13 | −24 db |
| P6 | −10 db | P14 | −26 db |
| P7 | −12 db | P15 | −28 db |
| P8 | −14 db | P16 | −30 db |

G. Output Circuit

As set forth supra, in the preferred embodiment of the apparatus of the invention, output circuit 21 includes two separate channels each having independently variable gain. Referring to FIG. 13, each channel of output circuit 21 of the preferred embodiment includes the following components:

| Component Name | Reference Number | Preferred Type or Value |
|---|---|---|
| Operational Amplifier | 443 | 741 |
| NPN Transistor | 445 | 2N4123 |
| PNP Transistor | 447 | 2N4125 |
| Diode | 449 | 1N914 |
| Diode | 451 | 1N914 |
| Resistor | 453 | 1.5 Kohm |
| Resistor | 455 | 1.5 Kohm |
| Resistor | 457 | 3.9 ohm |
| Resistor | 459 | 3.9 ohm |

Each channel of output circuit 21 of the preferred embodiment further includes divider switch 461 and single-pole, single-throw, momentary action switch 463.

One of the terminals of switch 463 constitutes input $I_O$ of the channel of output circuit 21 and is connected to output $O_M$ of mixer circuit 19. The other terminal of switch 463 is connected to input I of divider switch 461. Output O of divider switch 461 is connected to the non-inverting input of amplifier 433. The output of amplifier 433 is connected to the anode of diode 451 and to the cathode of diode 449. The cathode of diode 451 is connected to one end of resistor 453 and to the base of transistor 445. The other end of resistor 453 and the collector of transistor 445 are connected to $+V_{cc}(B)$.

The anode of diode 449 is connected to the base of transistor 447 and to one end of resistor 455. The other end of resistor 455 and the collector of transistor 447 are connected to $-V_{cc}(B)$. The emitters of transistors 445, 447 are connected to one end of resistors 457, 459, respectively. The other ends of resistors 457, 459 are connected together and constitutes output $O_O$ of the channel of output circuit 21. The inverting input of amplifier 443 is connected to output $O_O$.

In accordance with the configuration of a channel of output circuit 21 of the preferred embodiment as just described, amplifier 473 and transistors 475, 477 are wired as a unity gain buffer amplifier that provides increased current capabilities to the signal applied to the non-inverting input of amplifier 473. In this way, the signal at $O_0$ can be used to drive the transducer of an earphone of a typical headset used in audiometric evaluation. The actual sound pressure level (SPL) produced by such a transducer can be controlled by adjusting divider switch 461, the maximum SPL being generated when divider switch 461 is in position P$\phi$ and the minimum SPL being generated when divider switch 461 is in position P15. Thus, a sound of a particular SPL will be produced by the transducer connected to output $O_O$ by depressing switch 463.

In order to facilitate the description of the overall operation of the preferred embodiment of the apparatus of the invention, the components and outputs of the two channels will be differentiated by the additional letters "L" (for left) and "R" (for right).

3. Overall Operation

According to the overall operation and use of the preferred embodiment of the apparatus of the invention, such apparatus will produce electrical signals at $O_{OL}$ and $O_{OR}$ whose frequency spectrums, including both fundamental and harmonics, loudness (or sound pressure level) and duration can be varied by an operator. Thus, by connecting the right and left earphones of a binaural headset to $O_{OR}$ and $O_{OL}$, respectively, of output circuit 21, sounds of variable pitch, loudness, quality and duration can be produced.

Specifically, the pitch, or fundamental (F0) of such sound is variable between 125 Hz, which is selected by at least momentarily closing the switch of latching circuit 289, and 250 Hz, which is selected by closing the switch of latching circuit 291.

The quality of the sound is variable over three frequency ranges substantially corresponding to the lower three frequency regions of prominence in the speech sounds as observed in the outside air, i.e., the first three formants, hereinafter referred to as F1, F2 and F3. More particularly, the quality of such sound may be varied by varying the center frequencies of the filters of formant filter circuit 13, which is variable within F1, formant filter circuit 15, which is variable within F2, and formant filter circuit 17, which is variable within F3, and by adjusting the relative positions of the switches of resistor switch circuits 437, 438, 439, in accordance with the description of the formant filter circuits and the mixing circuit, supra.

The loudness of the sound produced by the right and left earphones is controlled by varying the position of divider switches 461R, 461L, respectively. In this regard, the apparatus may be calibrated by adjusting potentiometer 433 of mixing circuit 19 so that when the sound produced has only one harmonic having a 0 db gain applied by mixing circuit 19, i.e., when the position of the switch of one of resistor switch circuits 437, 438, 439 is P1 and the position of the switches of the other two of resistor switch circuits 437, 438, 439 is P0, and divider switches 461L, 461R are at position P0, the SPL of the sound produced by each earphone of the headset is 80 db. In this way, as divider switches 461L, 461R are moved from position P0 to position P16, the SPL of the sound produced by the left and right earphones, respectively, will be decreased 5 db for each position change. It should be noted that such calibration is applicable only when the sound produced has only one harmonic with a 0 db gain applied by mixing circuit 19.

The duration of the sound produced by the left and right earphones is controllable through switches 463L, 463R, respectively, the sound being produced whenever and for as long as such switches are closed.

4. Method of the Invention

It has been found that information significant to an assessment of a person's hearing can be obtained by determining such person's sensitivity to sounds similar to those he produces in his own speech. The apparatus of the present invention is well adapted for such a determination in that it is capable of producing sounds of variable pitch and quality. More specifically, the pitch of the sounds produced by the apparatus of the invention are variable between a frequency corresponding substantially to the average frequency of the fundamental of the speech of adult men, i.e., 125 Hz, and a frequency corresponding substantially to the average frequency of the fundamental of the speech of women and children. Furthermore, the harmonics of the sound produced by such apparatus are variable within F1, F2 and F3.

In particular, the preferred embodiment of the apparatus of the invention is capable of producing vowel sounds similar to those produced by an adult male or by women and children. Thus, when 125 Hz is selected as the fundamental frequency by closing the switch of latching circuit 289, vowel sounds similar to those produced by the speech of an average adult male can be produced by the apparatus by closing the control switch of one of the latching circuits of each of formant filter circuits 13, 15, 17, the particular latching circuit of each filter circuit whose control switch is closed to produce a particular vowel sound being as follows:

| Vowel Sound | Circuit 13 | Circuit 15 | Circuit 17 |
| --- | --- | --- | --- |
| i | 348 | 354 | 416 |
| I | 349 | 354 | 415 |
| ɛ | 350 | 353 | 415 |
| æ | 353 | 352 | 415 |
| a | 354 | 350 | 415 |
| ɔ | 352 | 348 | 415 |
| o | 350 | 348 | 415 |
| ʊ | 349 | 348 | 414 |
| u | 348 | 348 | 414 |
| ʌ | 351 | 349 | 414 |
| ɝ | 350 | 350 | 413 |

Similarily, where 250 Hz is selected as the fundamental frequency by closing the switch of latching circuit 291, vowel sounds similar to those produced by the speech of women and children can be produced by the apparatus by closing the control switch of one of the latching circuits of each of formant filter circuits 13, 15, 17, the particular latching circuit of each filter circuit whose control switch is closed to produce a particular vowel sound being as follows:

| Vowel Sound | Circuit 13 | Circuit 15 | Circuit 17 |
| --- | --- | --- | --- |
| i | 348 | 355 | 417 |
| I | 350 | 355 | 416 |
| ɛ | 352 | 354 | 417 |
| æ | 354 | 352 | 416 |
| a | 354 | 350 | 416 |
| ɔ | 352 | 349 | 414 |
| o | 350 | 349 | 413 |
| ʊ | 350 | 350 | 414 |
| u | 348 | 349 | 413 |
| ʌ | 352 | 350 | 416 |
| ɝ | 350 | 351 | 413 |

5. Summary

Although the apparatus and method described in detail supra has been found to be most satisfactory and preferred, many variations in structure and technique are possible. For example, a saw-tooth waveform generator may be substituted for signal generator 227. In this regard, it should be noted that the square-wave generated by signal generator 227 creates transients that are capable of stimulating the entire cochlear partition. As a result, frequency-specific information may not be available. The rise time of the saw-tooth waveform will substantially reduce the generation of such transients. Also, if a saw-tooth waveform is used, the apparatus may include a device for varying the rise time of such waveform. Such variable rise time will enable the operator to vary onsets influencing vowels in context of glide to plosive continuum. Also, additional amplification may be provided to increase the maximum SPL that can be produced by the apparatus. In addition, circuitry may be provided that will permit splitting the formants into the left and right earphones; for instance, the signal including one formant of a vowel sound would be directed to the right earphone and a signal including the other two formants of that vowel sound would be directed into the left earphone. Such splitting would enable testing of upward spread of masking out of the lower formants or fusion of signal capability in individuals with possible central auditory deficits. Furthermore, the apparatus may be ac-powered rather than battery-powered. Also, circuitry could be included to control the duration of a signal, i.e., the length of time that switches 463L, 463R are closed. If such circuitry is provided, the length of time of each signal could be made variable. In addition, 463L, 463R could be ganged so as to produce simultaneous operation.

Because many varying and different embodiments may be made within the scope of the inventive concept herein taught and because many modifications may be made in the embodiment herein detailed in accordance with the descriptive requirements of the law, it should be understood that the details herein are to be interpreted as illustrative and not in a limiting sense.

APPENDIX

Pin Connections for Integrated Circuits 1. 1458 Dual Operational Amplifier
Power: $+V_{cc}(B)$ pin 8; $-V_{cc}(B)$: pin 4
Amp #1:
  inverting input: pin 2
  non-inverting input: pin 3 output: pin 1
Amp #2:
  inverting input: pin 6
  non-inverting input: pin 5
  output: pin 7
2. 747 Dual Operational Amplifier
Power: +$V_{cc}$(B): pins 9, 12; −$V_{cc}$(B): pin 4
Amp #1:
  inverting input: pin 1
  non-inverting input: pin 2
  output: pin 12
Amp #2:
  inverting input: pin 7
  non-inverting input: pin 6
  output: pin 10
3. 741 Operational Amplifier
Power: +$V_{cc}$(B): pin 7; −$V_{cc}$(B): pin 4
  inverting input: pin 2
  non-inverting input: pin 3
  output: pin 9
4. LM324 Quad Comparator
Power: +$V_{cc}$(B): pin 4; −$V_{cc}$(B): pin 11
Comparator #1:
  "−" input: pin 2
  "+" input: pin 3
  output: pin 1
Comparator #2:
  "−" input: pin 6
  "+" input: pin 5
  output: pin 7
Comparator #3:
  "−" input: pin 9
  "+" input: pin 10
  output: pin 8
Comparator #4:
  "−" input: pin 13
  "+" input: pin 12
  output: pin 14
5. 4049 Hex Inverting Buffer
Power: +$V_{cc}$(B): pin 1; −$V_{cc}$(B): pin 8
Inverter #1:
  input: pin 3
  output: pin 2
Inverter #2:
  input: pin 5
  output: pin 4
Inverter #3:
  input: pin 7
  output: pin 6
Inverter #4:
  input: pin 9
  output: pin 10
Inverter #5:
  input: pin 11
  output: pin 12
Inverter #6:
  input: pin 14
  output: pin 15
6. 4011 Quad 2-input NAND Gate
Power: +$V_{cc}$(B): pin 14; −$V_{cc}$(B): pin 7
Gate #1:
  input: pins 1, 2
  output: pin 3
Gate #2:
  input: pins 5, 6
  output: pin 4
Gate #3:
  input: pins 8, 9
  output: pin 10
Gate #4:
  input: pins 12, 13
  output: pin 11
7. 4068 8-input NAND Gate
Power: +$V_{cc}$(B): pin 14; −$V_{cc}$(B): pin 7
Input: pins 2, 3, 4, 5, 9, 10, 11, 12
Output: pin 13
8. 4043 Quad NOR S/R Latch
Power: +$V_{cc}$(B): pin 16; −$V_{cc}$(B): pin 8
Enable (Pin 5) tied to +$V_{cc}$(B)
Latch #1:
  set input: pin 4
  reset input: pin 3
  Q output: pin 2
Latch #2:
  set input: pin 6
  reset input: pin 7
  Q output: pin 9
Latch #3: set input: pin 12
  reset input: pin 11
  Q output: pin 10
Latch #4:
  set input: pin 14
  reset input: pin 15
  Q output: pin 19. 4066 Quad Bilateral
9. Switch
Power: +$V_{cc}$(B): pin 14; −$V_{cc}$(B): pin 7
Switch #1:
  I/O terminals: pins 1, 2
  control input: pin 13
Switch #2:
  I/O terminals: pins 3, 4
  control input: pin 5
Switch #3:
  I/O terminals: pins 8, 9
  control input: pin 6
Switch #4:
  I/O terminals: pins 10, 11
  control input: pin 12
10. 8038 Signal Generator
Power: +$V_{cc}$(C): pin 6; −$V_{cc}$(C): pin 11
DC/FC: pins 4, 5
FM Bias: pin 7
FM Input: pin 8
$C_f$: pin 10
Sin Adj: pin 12
Sine Out: pin 2
Triangle Out: pin 3
Square out: pin 9
11. LM555 Timer
Power: +$V_{cc}$(C) pin 8; Gnd pin 1
Trigger input: pin 2
Output: pin 3
React: pin 4
Control: pin 5
Threshold: pin 6
Discharge: pin 7

I claim:

1. Apparatus for audiometric assessment using the formant frequencies for average voices of various identifiable groups of people, comprising:
   signal generation means for producing a first signal of selectably variable frequency; and
   filter means for converting a first signal into a complex second signal including (1) a fundamental component of frequency equal to the frequency of the first signal and (2) at least a first harmonic term of such first signal as a speech-type synthesized vowel sound.

2. Apparatus of claim 1 wherein the frequency of said first signal is variable among frequencies substantially corresponding to the average frequency of the fundamental of speech sounds produced by various identifiable groups of people.

3. Apparatus of claim 2 wherein the frequency of said first harmonic term is variable over a range substantially corresponding to the range of frequencies covered by the first three formants for average voices of adult men, women and children.

4. Apparatus of claim 2 wherein said second signal further includes a second harmonic term of selectably variable frequency.

5. Apparatus of claim 4 wherein the amplitudes of each of said first and second harmonic terms is separately variable.

6. Apparatus of claim 4 wherein the frequency of said first harmonic term is variable over a first range of frequencies substantially corresponding to one formant for average voices and the frequency of said second harmonic term is variable over a second range of frequencies substantially corresponding to another formant for average voices.

7. Apparatus of claim 6 wherein said first frequency is variable between 125 Hz and 250 Hz, said first range of frequencies extends from 250 Hz through 1250 Hz, and said second range of frequencies extends from 875 Hz through 2500 Hz.

8. Apparatus of claim 4 wherein said second signal further includes a third harmonic term.

9. Apparatus of claim 8 wherein the amplitude of each of said first, second and third harmonic terms is separately variable.

10. Apparatus of claim 8 wherein the frequency of said first harmonic term is variable over a first range of frequencies substantially corresponding to a first formant for average voices, the frequency of said second harmonic term is variable over a second range of frequencies substantially corresponding to a second formant for average voices, and the frequency of said third harmonic term is variable over a third range of frequencies substantially corresponding to a third formant for average voices.

11. Apparatus of claim 10 wherein said first frequency is variable between approximately 125 Hz and approximately 250 Hz, said first range of frequencies extends from approximately 250 Hz through approximately 1250 Hz, said second range of frequencies extends from approximately 875 Hz through 2500 Hz, and said third range of frequencies extends from approximately 2000 Hz through approximately 4000 Hz.

12. Apparatus of claim 1 wherein the frequency of said first signal is variable between a first frequency substantially corresponding to the average frequency of the fundamental of speech sounds produced by women and children and a second frequency substantially corresponding to the average frequency of the fundamental of speech sounds produced by adult men.

13. Apparatus of claim 12 wherein the frequency of said first harmonic term is variable over a range substantially corresponding to the range of frequencies covered by the first three formants for average voices.

14. Apparatus of claim 12 wherein said second signal further includes a second harmonic term of selectably variable frequency.

15. Apparatus of claim 14 wherein the amplitude of each of said first and second harmonic terms is separately variable.

16. Apparatus of claim 14 wherein said the frequency of said first harmonic term is variable over a first range of frequencies substantially corresponding to one formant for average voices and the frequency of said second harmonic term is variable over a second range of frequencies substantially corresponding to another formant for average voices.

17. Apparatus of claim 16 wherein said first frequency is variable between 125 Hz and 250 Hz, said first range of frequencies extends from 250 Hz through 1250 Hz and said second range of frequencies extends from 875 Hz through 2500 Hz.

18. Apparatus of claim 14 wherein said second signal further includes a third harmonic term.

19. Apparatus of claim 18 wherein the frequency of said first harmonic term is variable over a first range of frequencies substantially corresponding to a first formant for average voices, the frequency of said second harmonic term is variable over a second range of frequencies substantially corresponding to a second formant for average voices and the frequency of said third harmonic term is variable over a third range of frequencies substantially corresponding to a third formant for average voices.

20. Apparatus of claim 19 wherein said first frequency is variable between approximately 125 Hz and approximately 250 Hz, said first range of frequencies extends from approximately 250 Hz through approximately 1250 Hz, said second range of frequencies extends from approximately 875 Hz through 2500 Hz, and said third range of frequencies extends from approximately 2000 Hz through approximately 4000 Hz.

21. Method for assessment of a person's hearing using the formant frequencies for average speech sound of various identifiable groups of people, comprising the steps of:
generating a first signal having a fundamental component and substantially all the harmonics of such fundamental component; and
filtering a plurality of the harmonic components from such first signal so as to produce a second signal having the frequency and amplitude characteristics of a speech sound as a speech-type synthesized vowel sound.

22. Method of claim 21 wherein the filtering step includes passing only harmonics falling within one of the first three formants of an average speech sound.

23. Method of claim 21 wherein the filtering step includes passing a first harmonic falling within the first formant of a speech sound, passing a second harmonic falling within the second formant of a speech sound and passing a third harmonic falling within the third formant of a speech sound.

24. Methods of claim 23 wherein said filtering step includes separately varying the amplitudes of each of said first, second and third harmonics in said second signal.

25. Method of claim 24 wherein said amplitude varying step includes varying said amplitudes between $\phi$ and a non-zero value.

26. Method of claim 21 wherein the frequency of said first signal is varied such that it corresponds substantially to the frequency of the fundamental of the speech sounds of such person.

27. Method for assessment of a person's hearing comprising the steps of:
- generating a first signal having a fundamental component and substantially all the harmonics of such fundamental component; and
- filtering a plurality of the harmonic components from such first signal so as to produce a second signal having the frequency characteristics of a speech sound;
- the filtering step including passing a first harmonic falling within the first formant of a speech sound, passing a second harmonic falling within the second formant of a speech sound and passing a third harmonic falling within the third formant of a speech sound and separately varying the amplitudes of each of said first, second and third harmonics in said second signal, wherein said amplitude varying step includes varying said amplitudes between 0 and a non-zero value and wherein the amplitudes of said first, second and third harmonics in said second signal are separately varied so as to produce a synthetic vowel sound.

28. Method of claim 27 wherein the frequency of said first signal is varied such that it corresponds substantially to the frequency of the fundamental of the speech sounds of such person.

* * * * *